United States Patent
Rashad et al.

(10) Patent No.: US 7,013,898 B2
(45) Date of Patent: Mar. 21, 2006

(54) NASAL PRESSURE SENSOR OXYGEN THERAPY DEVICE

(75) Inventors: M. Abdul-Aziz Rashad, Kenmore, NY (US); Paul W. Belanger, East Amherst, NY (US); Bryan R. Bielec, Hamburg, NY (US)

(73) Assignee: Praxair Technology, Inc., Danbury, CT (US)

( * ) Notice: Subject to any disclaimer, the term of this patent is extended or adjusted under 35 U.S.C. 154(b) by 43 days.

(21) Appl. No.: 10/886,559

(22) Filed: Jul. 9, 2004

(65) Prior Publication Data

US 2006/0005842 A1    Jan. 12, 2006

(51) Int. Cl.
*A61M 15/08* (2006.01)
*A62B 9/06* (2006.01)
*A61B 5/08* (2006.01)

(52) U.S. Cl. ............ 128/207.18; 600/538; 128/203.22

(58) Field of Classification Search .......... 128/203.22, 128/204.21, 204.26, 207.18; 600/532, 538
See application file for complete search history.

(56) References Cited

U.S. PATENT DOCUMENTS

| | | | | | |
|---|---|---|---|---|---|
| 4,054,133 | A | * | 10/1977 | Myers ................... | 128/204.26 |
| 4,989,599 | A | * | 2/1991 | Carter ................... | 128/207.18 |
| 5,046,491 | A | * | 9/1991 | Derrick ................. | 128/200.24 |
| 5,137,017 | A | * | 8/1992 | Salter ................... | 128/207.18 |
| 5,280,780 | A | * | 1/1994 | Abel ..................... | 128/203.14 |
| 5,365,922 | A | | 11/1994 | Raemer ................ | 128/204.23 |
| 5,682,877 | A | | 11/1997 | Mondry ................ | 128/204.23 |
| 5,865,174 | A | | 2/1999 | Kloeppel ............... | 128/204.23 |
| 6,186,142 | B1 | | 2/2001 | Schmidt et al. ........ | 128/204.23 |
| 6,192,883 | B1 | | 2/2001 | Miller, Jr. ............. | 128/204.21 |
| 6,371,114 | B1 | | 4/2002 | Schmidt et al. ........ | 128/204.23 |
| 6,470,885 | B1 | | 10/2002 | Blue et al. ............. | 128/204.18 |
| 6,532,958 | B1 | | 3/2003 | Buan et al. ............ | 128/204.23 |
| 6,551,384 | B1 | | 4/2003 | Ackley et al. ......... | 95/96 |
| 6,629,525 | B1 | | 10/2003 | Hill et al. .............. | 128/202.26 |
| 6,655,385 | B1 | * | 12/2003 | Curti et al. ............ | 128/207.18 |

FOREIGN PATENT DOCUMENTS

WO    WO02056931 A2    1/2002

OTHER PUBLICATIONS

Fussell, et al. "Assessing Need for Long-Term Therapy: A Comparison of Conventional Evaluation and Measures of Ambulatory Oximetry Monitoring", *Respiratory Care* Feb. 2003 vol. 48 No. 2.

John C. Chaney, et al. "Implementation of an Oxygen Therapy Clinic to Manage Users of Long-term Oxygen Therapy" *Chest*/122/5/Nov. 2002.

* cited by examiner

*Primary Examiner*—Henry Bennett
*Assistant Examiner*—Dinnatia Doster-Greene
(74) *Attorney, Agent, or Firm*—Mary Raynor Jimenez

(57) ABSTRACT

Method and apparatus for supplying respiratory oxygen to a patient where the oxygen flow is monitored so as to control and conserve oxygen in response to the pressure in the nasal passages of the patient.

21 Claims, 1 Drawing Sheet

NASAL PRESSURE SENSOR OXYGEN THERAPY DEVICE

FIELD OF THE INVENTION

The invention relates to devices and methods using nasal pressure sensors for monitoring and effectively conserving the delivery of oxygen to a patient.

BACKGROUND OF THE INVENTION

In the US today there exists approximately 1 million people who suffer from chronic hypoxemia as a result of having a chronic obstructive pulmonary disease (COPD). Presently there is no cure for this condition, however the detrimental impact of chronic hypoxemia is mitigated by the prescription of long term oxygen therapy (LTOT). The continuous inhalation of low flows of oxygen, typically 2–3 lpm, from a nasal cannula increases the concentration of oxygen that the patient is breathing. It is estimated that for each 1 lpm (liter per minute) flow, the overall inhaled concentration rises by 3–4%. The increase in oxygen concentration compensates for the poor function of the patient's lungs in absorbing the oxygen.

Generally when a patient is diagnosed with chronic hypoxemia, oxygen is prescribed at a fixed flow rate based on a 20 minute titration in the doctor's office. During the test, the patient's blood oxygen saturation is measured by either using an invasive blood gas analyzer or a non-invasive device known as the pulse oximeter. While measuring the blood saturation ($SpO_2$), the patient may be asked to walk on a treadmill so as to measure their need for supplemental oxygen while exerting themselves. Based on this brief test, a fixed flow of oxygen is prescribed. The patient may be advised to increase the flow rate of oxygen during the exertion, for example while climbing stairs, while sleeping or if they feel short of breath. In many cases the patient is just prescribed a flow rate of 2 lpm and then asked to come back if they continue to feel the side effects of hypoxemia which can manifest themselves as shortness of breath, headaches, nausea, etc.

Patients may be prescribed oxygen to breathe 24 hours per day or may only require oxygen while ambulating. If a patient needs to breathe oxygen even while resting, they will be given a stationary oxygen generating unit in their home which can be set to produce 0 to 5 lpm of 93% oxygen. Generally, the units today are manually set by the patient to the prescribed flowrate. If a patient requires oxygen while ambulating, they will typically carry small high pressure oxygen cylinders or small refillable liquid oxygen dewars. Recently, small portable oxygen generators have also been introduced into the market but they suffer from drawbacks of being significantly heavier and short battery life. These devices also would be manually set by the patient to deliver oxygen at the prescribed flow rate. Due to the expense of providing oxygen in small cylinders as well as dewars for ambulation, the need to conserve the oxygen flow and efficiently utilize what was available was addressed by the development of oxygen conserving devices. These devices only deliver short pulses of oxygen at the beginning of the patients inhalation. By not delivering oxygen during exhalation or the later period of inhalation, the oxygen which would have had no impact on increasing the patient's oxygen saturation is conserved. There now exists both pneumatic and electronic oxygen conserving devices which can achieve oxygen conserving ratios from 2:1 to 6:1 compared to the delivery of continuous oxygen flow. The higher conservation ratios can only be achieved by the electronic devices since they can be programmed to skip breaths so that oxygen pulse is only delivered every other breath. Electronic devices cannot be used on all ambulating patients since their high conservation ratios can actually result in poor oxygen saturation for the patient particularly during periods of high amublation.

Pressure sensing of the onset of inhalation in electronic oxygen conservers is currently done in one of two ways:

1. Some designs require that a dual lumen cannula is used in which one of the lumens is dedicated to pressure sensing while the other is dedicated to the supply of oxygen. This design is meant to be more sensitive to the onset of inhalation but suffers from the drawback of only being able to deliver oxygen to one of the nasal passages.

2. Other designs will use a single lumen cannula that typically have a pressure sensor connected to the T piece below the two nasal prongs. Overall pressure drop associated from inhalation is sensed from both nasal passages and oxygen is then delivered to both nasal passages.

Both designs suffer from the drawback that if one of the patient's nasal passages is blocked, it will interfere with the detection and delivery of oxygen.

The idea of continuous oxygen flow adjustment to maintain patient saturation has existed for over 50 years. U.S. Pat. No. 2,414,747 by Kirschbaum (1947) discloses a method and apparatus for controlling oxygen content of the blood of living animal. The method used an ear oximeter, which produced a signal to control the fraction of inspired oxygen (F102).

U.S. Pat. No. 4,889,116 by Taube in 1986 describes an adaptive controller, which utilizes a pulse oximeter to measure blood oxygen saturation ($SpO_2$). This measurement would be used to calculate the necessary F102 to maintain a preset saturation level.

U.S. Pat. No. 5,365,922 by Raemer describes a closed loop non-invasive oxygen saturation control system which uses an adaptive controller for delivering a fractional amount of oxygen to a patient. Features of the control algorithm include a method for recognizing when pulse oximeter values deviate significantly from what should be expected. At this point the controller causes a gradual increase in the fractional amount of oxygen delivered to the patient. The feedback control means is also disconnected periodically and the response of the patient to random changes in the amount of oxygen delivered is used to tune the controller response parameters.

U.S. Pat. No. 5,682,877 describes a system and method for automatically selecting an appropriate oxygen dose to maintain a desired blood oxygen saturation level is disclosed. The system and method are particularly suited for use with ambulatory patients having chronic obstructive lung disease or other patients requiring oxygenation or ventilation. In one embodiment, the method includes delivering a first oxygen dose to the patient while repeatedly sequencing through available sequential oxygen doses at predetermined time intervals until the current blood oxygen saturation level of the patent attains the desired blood oxygen saturation levels. The method then continues with delivering the selected oxygen dose to the patient so as to maintain the desired blood oxygen saturation level.

U.S. Pat. No. 6,192,883 B1 describes an oxygen control system for supplying a predetermined rate of flow from an oxygen source to a person in need of supplemental oxygen comprising in input manifold, an output manifold and a plurality of gas conduits interconnecting the input manifold to the output manifold. The oxygen source is arranged in flow communication with the input manifold, and a needle valve is positioned in flow control relation to each of the conduits so as to control the flow of oxygen from the input manifold to the output manifold. A plurality of solenoid valves, each having a first fully closed state corresponding to a preselected level of physical activity of the person and a second, fully open state corresponding to another preselected level of physical activity of the person, are positioned in flow control relation to all but one of the conduits. Sensors for monitoring the level of physical activity of the person are provided, along with a control system that is responsive to the monitored level of physical activity, for switching the solenoids between the first state and the second state. A method for supplying supplemental oxygen to a person according to the level of physical activity undertaken by that person is also provided.

World Patent application No. WO 02/056931 A2 by Tyomkin et al. describes a method for controlling flow of gas to a patient by measuring of a preselected dissolved substance in the blood stream of a patient. The amount of gas is regulated to maintain the preselected dissolved substance above a desired value.

All the patents discussed above are based on controlling a continuous flow of oxygen. There are also patents which have described control algorithms for pulse dose oxygen devices such as the oxygen conserver.

U.S. Pat. No. 6,470,885 B1 describes a method and apparatus for controlling oxygen delivery to a person is disclosed. In one embodiment, the method includes receiving a goal blood-oxygen saturation level, measuring an actual saturation level of the person, determining a breath rate of the person, sensing a period of inhalation by the person, and delivering oxygen during inhalation by moving a valve to an oxygen delivery position for a calculated period of time based upon the actual saturation level as compared to the goal level of the person's blood-oxygen content. One embodiment of an apparatus comprises an open-loop breathing system including a control valve for controlling the flow of oxygen from a source to the person, a pressure sensor for detecting a period of inhalation, an oximeter for measuring actual blood-oxygen saturation, and a processor for calculating the time the valve needs to be maintained in an open position to deliver oxygen.

U.S. Pat. No. 6,629,525 B2 describes a portable oxygen concentrator system adapted to be transported by a user. The portable oxygen concentrator system includes an energy source, an air separation device powered by the energy source and adapted to convert ambient air into concentrated oxygen gas for the user, at least one sensor adapted to sense one or more conditions indicative of the oxygen gas needs of the user, and a control unit interrelated with the air separation device and the at least one sensor to control the air separation device so as to supply an amount of oxygen gas equivalent to the oxygen gas needs of the user based at least in part upon the one or more conditions sensed by the at least one sensor.

U.S. Pat. No. 5,865,174 describes an apparatus which conserves oxygen delivered from a supply to a patient through a cannula by providing oxygen delivery selectively in accordance with the physiological requirements and current breathing pattern of the patient. Oxygen flow is set at a prescribed flow rate from the supply by a regulator. An oxygen conserving unit includes a controller that operates responsive to timed relationships among pressure signals determined by a fuzzy logic program to deliver oxygen to the patient by opening a valve when a sensed pressure in the patient's nasal passage reaches a threshold level and when the controller determines that the reaching of the threshold is indicative of an inhalation cycle. The controller is further operative to adjust the time period that oxygen is delivered to the patient in accordance with a programmed relation to meet the dynamically changing needs of the patient. The apparatus further includes features which provide fast response, conservation of the energy from a battery power source and both visual and audio indicators to provide indications of alert and alarm conditions. The apparatus further provides control by the user through a single manually actuated switch, and mechanical interconnection with the switch and valve to assure continuous flow when the switch is set to a continuous flow setting.

U.S. Pat. No. 6,532,958 B1 describes methods and systems for supplying supplemental oxygen to patients for use in sub-acute care which maintains healthy blood oxygen content in the patients by controlled dosing of oxygen with a measured response to the patient's actual blood oxygen content are disclosed. The dosing can be provided by simple ON/OFF control over the delivery of oxygen or the amount of oxygen delivered to the patient with each inhalation can be varied in response to the patient's need as determined by a more sophisticated control scheme, such as PID loop control algorithm, that utilizes the difference between the patient's actual blood oxygen content and a target blood oxygen content and/or trends in the blood oxygen content. The systems and methods are particularly directed at patients receiving supplemental oxygen in a sub-acute care environment.

U.S. Pat. No. 6,186,142 B1 describes methods and systems for supplying respiratory oxygen to patients when the patients are inhaling are disclosed. The methods and systems may rely on delivery devices that are selectively placed in fluid communication with either a respiration sensor or a source of oxygen. The methods and systems may actively monitor for exhalations, as well as monitor for oxygen in the oxygen source. The respiration sensor may preferable be a flow sensor.

U.S. Pat. No. 6,371,114 B1 describes methods and systems for supplying supplemental oxygen to patients for use in sub-acute care which maintains healthy blood oxygen content in the patients by controlled dosing of oxygen with a measured response to the patient's actual blood oxygen content are disclosed. The dosing can be provided by simple ON/OFF control over the delivery of oxygen or the amount of oxygen delivered to the patient with each inhalation can be varied in response to the patient's need as determined by a more sophisticated control scheme, such as PID loop control algorithm, that utilizes the difference between the patient's actual blood oxygen content and a target blood oxygen content and/or trends in the blood oxygen content. The systems and methods are particularly directed at patients receiving supplemental oxygen in a sub-acute care environment.

A major flaw with current oxygen generating devices is the fact that a patient's ideal need for oxygen varies with time both in the short term as a result of varying exertion and in the long term as result of improvement or deterioration in health. When a doctor prescribes a fixed flow rate of oxygen for a patient they are mainly concerned with ensuring that the patient's blood saturation does not drop below an $SpO_2$ value of 88%. They are not concerned if the patient is receiving too much oxygen, for example while resting. The prescription is therefore more likely to be conservative in nature so as to ensure oversaturation as opposed to undersaturation. It is generally believed and accepted by doctors that too much oxygen flow is harmless whereas too little can be harmful. This method of oxygen prescription is prone to error as proved by a recent study by Fussell et al. (Respiratory Care—February 2003, Vol. 48 No. 2). In this study, 20 patient's blood saturation levels were monitored continuously using pulse oximeters to confirm if their oxygen prescription adequately maintained their saturation. The conclusion of the study was that there was a poor relationship between conventional oxygenation assessment method and continuous ambulatory oximetry during LTOT screening with COPD patients.

Generally, after a second doctor visit which is typically scheduled 3 months after the prescription is initially made, patients may be asked to return to the doctor anywhere between 6 to 12 months. During that time if the patient's health and hence need for oxygen changes, a significant time may pass before it is detected by the doctor or home care provider.

Conservative (high) oxygen prescriptions, while they may be harmless to the patient, are needlessly expensive resulting in increase in the cost of providing oxygen for the home care provider as well as increase the hurdles that battery and oxygen separation technology have to overcome to develop a portable oxygen generating unit that can last a reasonable amount of time and weigh less than what is believed to be the upper acceptable limit of 10 lbs.

Many COPD patients who use stationary oxygen concentrators in their homes are financially impaired and are concerned about the power costs of continuously running an oxygen concentrator. In many cases this has led to a compliance issue where the patient refuses to switch on the concentrator and follow the therapy as prescribed by the doctor in order to save on their electricity bill. Current oxygen concentrator designs will typically produce the maximum flowrate possible which is typically 5 lpm. If a patient's resting prescription is 2 lpm, the patient will set a flow rate through their cannula to the required flow and the excess oxygen that is being produced is vented from the concentration into the room. There is potential to reduce power consumption by only producing the amount oxygen that the patient needs in a real time basis. Many oxygen therapy patients can spend a significant amount of their time while resting with blood saturation levels that are acceptable.

It is an object of the present invention to provide an oxygen delivery system which supplies oxygen flow at a rate that a patient needs on a real time basis as determined by the inhalation pressure in the nasal passages of the patients.

It is another object of the present invention to provide both a system and methods for optimal conserving of oxygen deliver to a patient using nasal pressure sensor means with an oxygen flow conserver.

With these and other objects in mind, the invention is hereinafter described in detail, the novel features thereof being particularly pointed out in the appended claims.

SUMMARY OF THE INVENTION

Another embodiment of the invention relates to a method for delivering and controlling oxygen to a patient from an oxygen supply which effectively conserves said oxygen supply, comprising the steps of:
an oxygen supply;
two delivery ports connected to two lumen cannulas with one lumen cannula adapted to be fitted within a right nasal passage of a patient and the other lumen cannula adapted to be fitted within a left nasal passage of a patient;
an oxygen conserver controller connected to a power supply means, the oxygen supply and the two delivery ports and having a first and second pressure sensor adapted for sensing an inhalation pressure separately from both the right and left nasal passages respectively, and comparing means for detecting the difference in the pressure level between the nasal passages of the patient and means for providing a control signal as to the level of the difference in the inhalation pressure in the nasal passages, and means for detecting and using the control signal to alter the delivery of oxygen from the oxygen supply to at least one of the nasal passages of the patient.

Another embodiment of the invention relates to a method for delivery and controlling oxygen to a patient from an oxygen supply which effectively conserving said oxygen supply, comprising the steps of:
a) providing a supply of oxygen;
b) providing pressure sensoring means for separately measuring the inhalation pressures in nasal passages of a patient;
c) measuring the different value in the inhalation pressure in each nasal passage of the patient and providing said measured value as a control signal; and
d) adjusting a deliverable amount of oxygen to at least one nasal passage of the patient in response to the control signal of step c).

Due to advances in pressure sensors and oxygen conservers technology, these devices can be very small in size and could be easily carried continuously by the patient.

Otyher embodiments to sense the difference in the obstruction between the nasal passage could be done using flow sensor, temperature sensor, vibration sensor and noise sensor.

The oxygen conservers could be a portable or stationary device where the power supplied to the conserver is varied and hence the amount of oxygen produced is directly linked to the patient's need for oxygen as measured by the pressure in the nasal passages of a patient. Since only the amount of oxygen required is generated, this unit may consume less power and thus last longer than existing portable units which consume a fixed amount of power independent of the amount of oxygen that the patient actually needs. Also during periods of exertion, this device will more adequately and automatically serve the patient's need for oxygen and hence prevent them from undesirable high exhaustions.

Varying the actual amount of oxygen produced as opposed to just adjusting the flow with a control valve whereby only a fraction of the produced oxygen is utilized could result in a waste of energy. For example, patients can breathe room air for significant periods of time while resting. During these periods the oxygen conserver will be effectively switched off to conserve power consumption.

BRIEF DESCRIPTION OF THE DRAWINGS

A preferred embodiment of the control delivery mechanism of the invention is illustrated in FIG. 1. With reference to FIG. 1, an electronic oxygen flow conserver 2 is shown that which will deliver oxygen flow upon the patient's inhalation to either both nasal passages or to only one of the nasal passages if the other passage is blocked or restricted in flow. This will ensure that the oxygen is delivered most effectively by minimizing the release of oxygen to a nasal passage which is blocked as well as delivering the oxygen as early as possible and as deep as possible into the patient's lungs.

Figure 1:
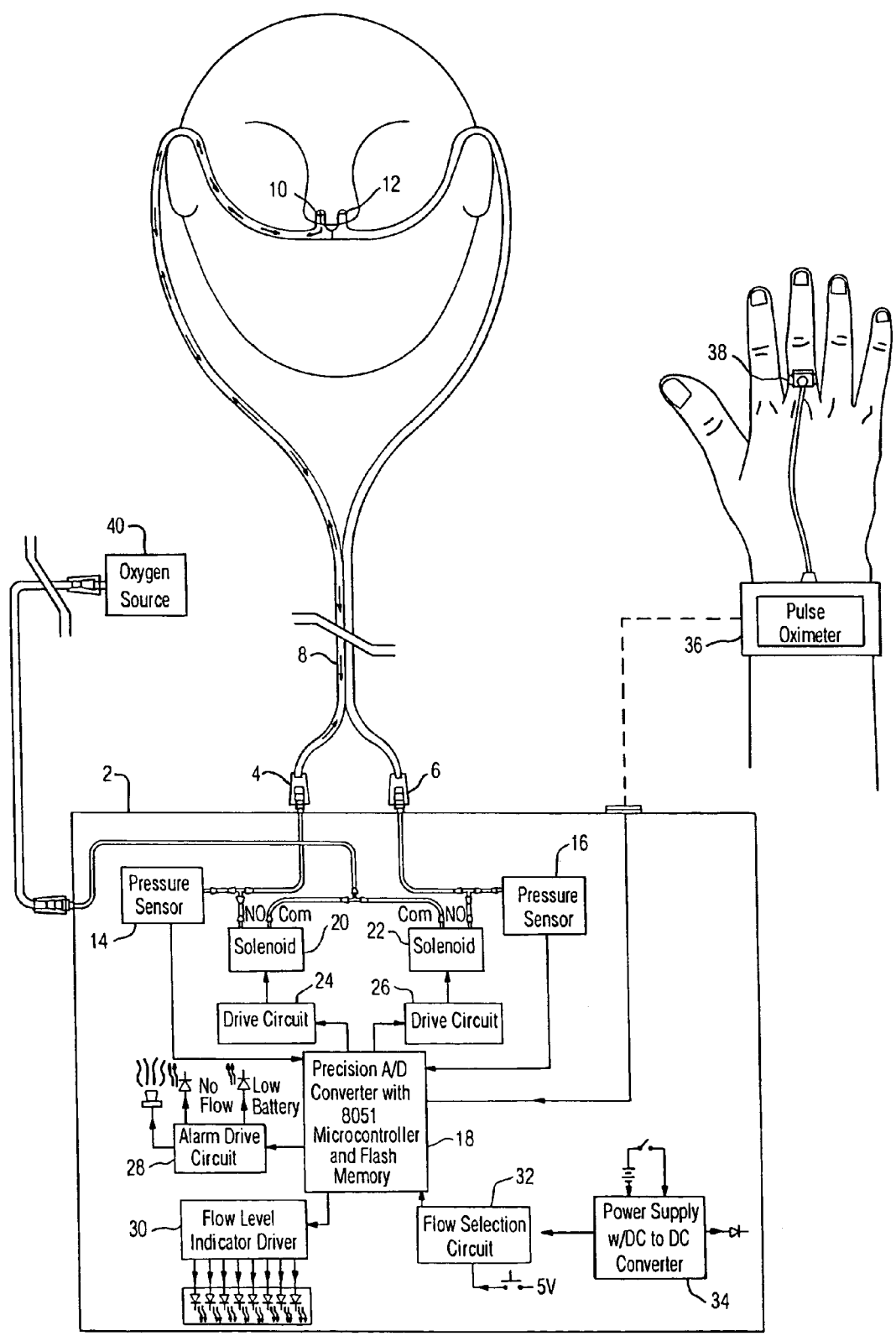
FIG. 1 is a block diagram of an embodiment of the present invention using dual nasal pressure sensors to control the flow of oxygen to a patient.

The oxygen conserving device 2 has two oxygen delivery ports 4 and 6. Delivery port 4 is connected to one lumen of a dual lumen cannula which would supply oxygen 40 to the patient's right nasal passage via nasal prong 10 of cannula 8. Delivery port 6 is connected to the second lumen of dual lumen cannula 8 so that it can only deliver oxygen to the patient's left nasal passage via nasal prong 12. Oxygen delivery ports 4 and 6 have conventional type pressure sensors 14 and 16, respectively, attached to sense the pressure of inhalation in either lumen port. The two signals produced downstream of the pressure sensors are then compared in a comparator circuit which is located in oxygen conserver microcontroller 18 to determine if there is a significant difference in inhalation pressure between the two nasal passages. Suitable conventional microcontrollers include, but are not limited to Model 8051 microcontroller and flash memory made by Texas Instruments; Model MSC 1210 made by Texas Instruments; and Part No. MSC 1210Y2PAGT-ND microcontroller made by Digi-Key Corporation.

If the difference between the two signals, X, is greater than a preset minimum value, Y, the controller 18 will only activate one of the conventional type solenoids 20 and 22, through conventional drive circuits 24 and 26 respectively. The solenoid activated will be the one which is delivering oxygen to the nasal passage which caused the larger pressure drop during inhalation. If the difference X is less than the present minimum Y, then the processor will allow both solenoids 20 and 22 to open so that oxygen is delivered to both nasal passages by activating both drive circuits 24 and 26. Preferably the pressure sensors should have an accuracy of +/-0.003 psi, so as to minimize the impact of signal inaccuracy as well as ensure that the difference measured is due to a real blockage value of the present minimum Y which will be in the range of 0.01–0.05 psi, preferable -0.02–0.04 psi.

The control algorithm for oxygen delivery could be conventionally designed so that the processor 18 makes a real time decision on which nasal passage to deliver oxygen to upon the onset of every breath. It could also be preferentially designed to periodically make an assessment of the pressure drops in each lumen so that it can periodically redirect flow of oxygen. For example the processor 18 could automatically switch on to make a comparison over a period of 10–20 seconds to determine if there is a nasal restriction. Based on this comparison it could re-direct oxygen flow and then switch off, only to switch on again to repeat the comparison after some time has elapsed, e.g. 30 minutes. This periodic assessment will have the advantage of conserving power consumed in the comparison. It will also reduce chances of erroneous sensor fluctuations from impacting the decision on oxygen delivery since a consistent difference between the two passages will have to be monitored over a number of breaths before the decision to redirect oxygen flow is made.

The conserver 2 has an alarm 28 to alert an user if the measured values of X exceeds or is below the normal expected range so as to alert the user that there may be an error with the pressure sensing mechanism of oxygen conserving device. As with conventional conserving devices, a flow level selector 30, a flow level indicator 32 and a power supply 34 are included.

The electronic conserver 2 could also be designed to receive inputs such as oxygen saturation and heart rate from a pulse oximeter 36. These inputs would be used in an algorithm to determine the correct flow rate of oxygen to be delivered to the patient. In this embodiment as shown in FIG. 1, the pulse oximeter 36 may be worn on the patient's wrist. The pulse oximeter probe 38 could be designed as a ring shaped device which is worn at the base of one of the patient's fingers. It is understood that this location is not an ideal place for sensing oxygen saturation as is a finger tip. However, in applications where the patient is expected to wear the pulse oximeter on a continuous basis, this location serves as a far more user friendly and practical place to have a probe which does not interfere with daily activities requiring the user's finger tips. The author believes that with advances in pulse oximetry as well as a new desire for continuous monitoring, pulse oximeter technology will advance to a point where ring shaped probes can be practically used.

Specific features of the invention are shown in one or more of the drawings for convenience only, as each feature may be combined with other features in accordance with the invention. Alternative embodiments will be recognized by those skilled in the art and are intended to be included within the scope of the claims.

What is claimed:

1. An apparatus with nasal pressure sensing means for automatically controlling and conserving the delivery of oxygen to a patient comprising:
    an oxygen supply;
    two delivery ports connected to two lumen cannulas with one lumen cannula adapted to be fitted within a right nasal passage of a patient and the other lumen cannula adapted to be fitted within a left nasal passage of a patient;
    an oxygen conserver controller connected to a power supply means, the oxygen supply and the two delivery ports having first and second pressure sensors adapted for sensing an inhalation pressure separately from both the right and left nasal passages, and comparing means for detecting the difference in the pressure level between the nasal passages of the patient and means for providing a control signal as to the level of the difference in the inhalation pressure in the nasal passages, and means for detecting and using the control signal to alter the delivery of oxygen from the oxygen supply to at least one of the nasal passages of the patient.

2. The apparatus of claim 1 wherein the oxygen conserver controller is a microcontroller with flash memory.

3. The apparatus of claim 1 wherein the means for detecting and using the control signal is a drive circuit coupled to a solenoid.

4. The apparatus of claim 2 wherein the microcontroller has a stored fixed signal value that is adapted to transmit the control signal only when the signal representing the difference in the pressure level between the nasal passages exceeds the stored fixed signal value.

5. The apparatus of claim 3 wherein the oxygen conserver controller is adapted to transmit the control signal to at least one solenoid in response to a signal in the pressure sensors which would indicate a blockage in at least one of the nasal passages.

6. The apparatus of claim 5 wherein the oxygen conserver is adapted to transmit the control signal to both solenoids when a signal representing both nasal passages block to an undesirable level.

7. The apparatus of claim 1 wherein the pressure sensors have an accuracy of about +/-0.003 psi.

8. The apparatus of claim 4 wherein the fixed signal value corresponds to a pressure level of between about 0.01 psi and about 0.05 psi.

9. The apparatus of claim 1 wherein alarm means are added to indicate any defaults in the signals.

10. The apparatus of claim 1 wherein oximeter means are coupled to the oxygen conserver controller and said oximeter means has a first non-invasion sensor to measure oxygen saturation and a second sensor to measure pulse rate.

11. A method for delivering and controlling oxygen to a patient from an oxygen supply which effectively conserves said oxygen supply, comprising the steps of:
 a) providing a supply of oxygen;
 b) providing pressure sensing means for separately measuring the inhalation pressures in nasal passages of a patient;
 c) measuring the difference in value in the inhalation pressure in each nasal passage of the patient and providing said measured value as a control signal; and
 d) adjusting a deliverable amount of oxygen to at least one nasal passage of the patient in response to the control signal of step c).

12. The method of claim 11 wherein the sensoring means in step b) are pressure sensors having an accuracy of about +/−0.003 psi.

13. The method of claim 11 wherein in step d) solenoids are used for adjusting the deliverable amount of oxygen to the nasal passages of the patient.

14. The method of claim 11 wherein after step a), the following steps are added:
 $a^1$) providing a setpoint pressure desired signal value; and
 after step c),
 the following step is added:
 $c^1$) measuring the difference in value between the setpoint pressure signal value from step $a^1$) and the control signal from step c) as a final control signal; and using the final control signal in place of the control signal in step d).

15. The method of claim 14 wherein in step $a^1$) the desired setpoint pressure signal corresponds to a pressure level of between about 0.01 psi and about 0.05 psi.

16. The method of claim 11 wherein the following steps are added after step d):
 e) measuring the oxygen saturation and providing said measured value as a saturation signal;
 f) measuring the pulse rate and providing said measured value as a pulse signal; and
 g) adjusting a deliverable amount of oxygen to the patient in response to the saturation signal and the pulse signal.

17. The method of claim 16 wherein the saturation signal and the pulse signal is provided using an oximeter.

18. The method of claim 11 wherein the following step is added:
 e) providing alarm means for indicating any default in any of the signals.

19. The method of claim 16 wherein the following step is added:
 h) providing alarm means for indicating any default in any of the signals.

20. An apparatus with nasal pressure sensing means for automatically controlling and conserving the delivery of oxygen to a patient comprising:
 an oxygen supply;
 two delivery ports connected to two lumen cannulas with one lumen cannula adapted to be fitted within a right nasal passage of a patient and the other lumen cannula adapted to be fitted within a left nasal passage of a patient;
 an oxygen conserver controller connected to a power supply means, the oxygen supply and the two delivery ports having at least one sensor adapted for sensing the difference in the obstruction between the right and left nasal passages and comparing means for detecting the difference in the obstruction level between the nasal passages of the patient and means for providing a control signal as to the level of the difference in the nasal passages, and means for detecting and using the control signal to alter the delivery of oxygen from the oxygen supply to at least one of the nasal passages of the patient.

21. The apparatus of claim 20 wherein the at least one sensor adapted for sensing the difference in the obstruction between the right and left nasal passages is selected from the group consisting of flow sensor, temperature sensor, vibration sensor and noise sensor.

* * * * *